United States Patent
Saito et al.

(10) Patent No.: US 7,205,396 B2
(45) Date of Patent: Apr. 17, 2007

(54) BENZODEAZAADENINE DERIVATIVE BASE AND ELECTRONIC MATERIAL CONTAINING THE SAME

(75) Inventors: Isao Saito, Kyoto (JP); Akimitsu Okamoto, Kyoto (JP); Kazuo Tanaka, Kyoto (JP)

(73) Assignee: Japan Science and Technology Agency, Saitama (JP)

( * ) Notice: Subject to any disclaimer, the term of this patent is extended or adjusted under 35 U.S.C. 154(b) by 383 days.

(21) Appl. No.: 10/508,138

(22) PCT Filed: Aug. 15, 2002

(86) PCT No.: PCT/JP02/08287

§ 371 (c)(1),
(2), (4) Date: Sep. 17, 2004

(87) PCT Pub. No.: WO03/078447

PCT Pub. Date: Sep. 25, 2003

(65) Prior Publication Data

US 2005/0142554 A1    Jun. 30, 2005

(30) Foreign Application Priority Data

Mar. 20, 2002    (JP)    .............. 2002-079803

(51) Int. Cl.
*C07H 21/00* (2006.01)
*C07H 21/02* (2006.01)
*C12Q 1/68* (2006.01)

(52) U.S. Cl. .................. 536/23.1; 536/24.3; 536/25.3; 435/6

(58) Field of Classification Search .............. 536/23.1, 536/24.3, 25.3; 435/6
See application file for complete search history.

(56) References Cited

FOREIGN PATENT DOCUMENTS

EP        0 369 360 A2    5/1990

OTHER PUBLICATIONS

International Search Report Dated Nov. 5, 2002.
Hubschwerlen et al., "Pyrimido [1,6-a]benzimidazoles: A New Class of DNA Gyrase Inhibitors," J. Med. Chem., vol. 35., No. 8, pp. 1385-1392, American Chemical Society (1992).

*Primary Examiner*—Jezia Riley
(74) *Attorney, Agent, or Firm*—Rader, Fishman & Grauer PLLC

(57) ABSTRACT

A nucleic acid base for hole transportation in DNAs which does not cause oxidative decomposition; and an artificial DNA molecule which can realize effective hole transportation in DNAs while maintaining the double spiral structure of the DNAs. Provided are: a nucleic acid which contains a benzodeazaadenine derivative base represented by the general formula (I):

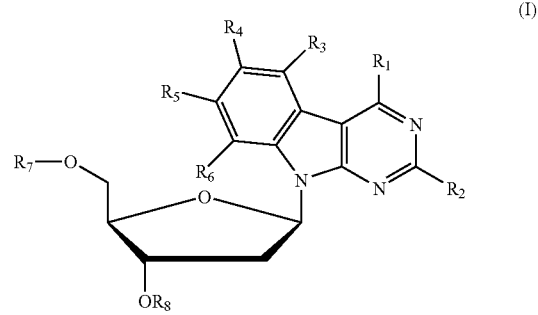

(wherein $R_1$, $R_2$, $R_3$, $R_4$, $R_5$, and $R_6$ each independently represents hydrogen, amino, mono (lower alkyl) amino, di (lower alkyl) amino, hydroxy, lower alkoxy, halogeno, cyano, mercapto, lower alkylthio, or aryl; and $R_7$ and $R_8$ each independently represents hydrogen or a group bonded to phosphoric acid);
and a polynucleotide comprising the nucleic acid.

7 Claims, 3 Drawing Sheets

BENZODEAZAADENINE DERIVATIVE BASE AND ELECTRONIC MATERIAL CONTAINING THE SAME

TECHNICAL FIELD

The present invention relates to a nucleic acid comprising a modified nucleic acid base that has charge transportability equal to that of guanine and is resistant to oxidative decomposition, a polynucleotide comprising the nucleic acid, and an electronic material comprising the polynucleotide.

BACKGROUND OF THE INVENTION

Many researches have been made on electronic materials utilizing natural DNAs. Conformation of higher-order structure of the natural DNAs can be easily controlled, whereby attention has been paid to the use of the natural DNAs as conductive molecular wires. It has been known that, although guanine (G) has the smallest oxidation potential among natural nucleic acid bases and can effectively mediate charge transport in the DNAs, oxidative decomposition of guanine occurs as a side reaction. On the other hand, adenine (A) is low in charge transport efficiency though resistant to the oxidative decomposition. Under the above-described circumstances, from the viewpoint of creating a next-generation molecular wire, development of a modified nucleic acid base, which has charge transportability equal to that of guanine and is resistant to the oxidative decomposition, is a very interesting research theme to provide a new material for the fields of nanotechnology as well as material science.

Thus, the present invention provides an artificial DNA, which has been expected to be used as a conductive nanowire.

DISCLOSURE OF THE INVENTION

The DNAs have many problems, and the main problem is deterioration due to the oxidative decomposition of the nucleic acid bases, particularly guanine. An object of the present invention is to solve the problem, thereby providing a nucleic acid base for hole transport in the DNAs, which does not cause the oxidative decomposition. A further object of the invention is to provide an artificial DNA molecule capable of achieving effective hole transport in the DNA while maintaining the double helix structure of the DNA.

BRIEF DESCRIPTION OF THE DRAWINGS

In FIG. 1, the abscissa represents time (second) of irradiation with 366 nm light, and the ordinate represents retention ratio (%) of the nucleic acids.

In FIG. 2, the longitudinal direction is direction of hole transport, X represents the base between the guanines (G), and Y represents a base complementary thereto. In the transverse direction in FIG. 2, the leftmost is a control (con), and the cases of X-Y of $^{BD}$A-cytosine (C), $^{BD}$A-thymine (T), guanine (G)-adenine (A), guanine (G)-cytosine (C), or adenine (A)-thymine (T) are shown at the right side thereof.

BEST MODE FOR CARRYING OUT THE INVENTION

Figure 1:
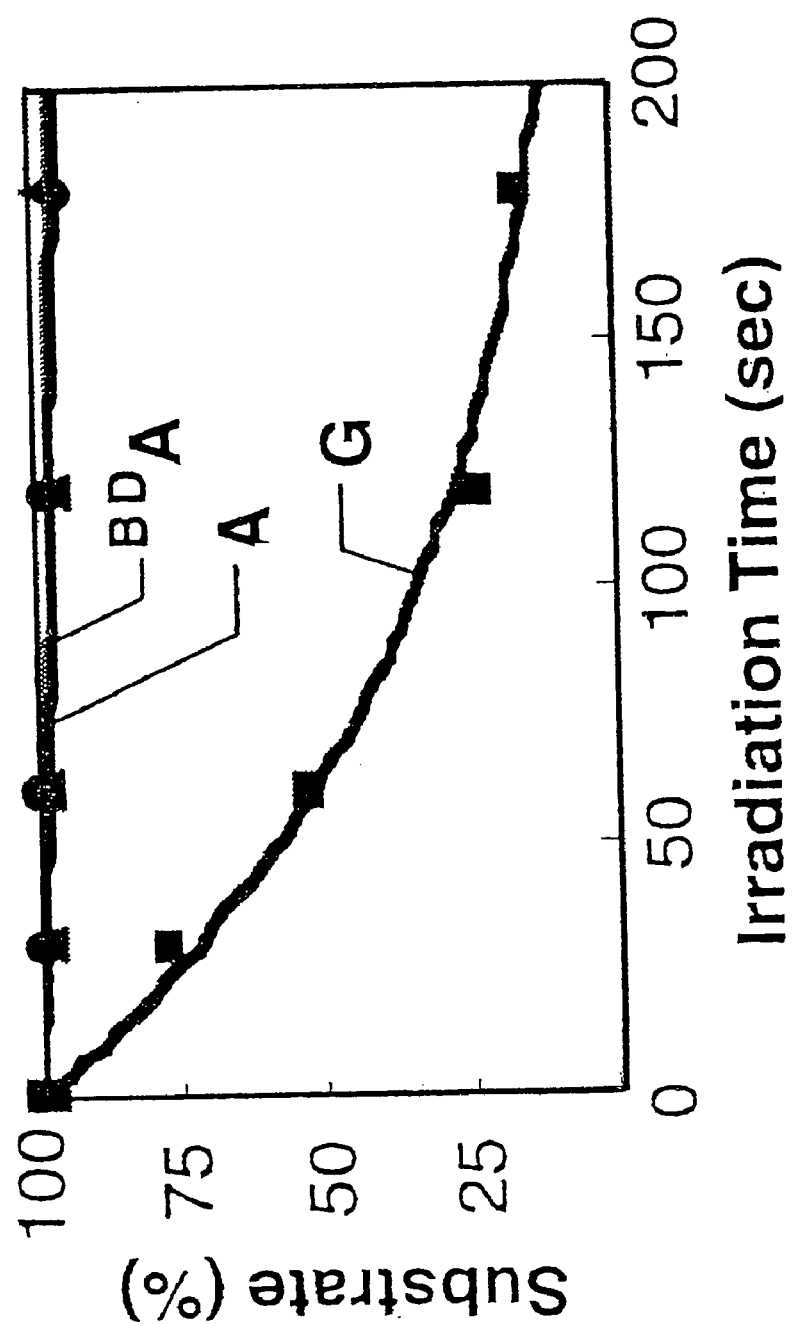
FIG. 1 shows results of testing an oxidative decomposition rate of a nucleic acid $^{BD}$A of the present invention in comparison with guanine (G) and adenine (A).

As a result of synthesizing various artificial bases and examining their antioxidant properties and hole transportabilities to solve the above problem, the inventors have found that suitable for the objects is a benzodeazaadenine obtained by condensing adenine with a benzene ring at the 7- and 8-positions to increase the charge transport efficiency due to expansion of the conjugated system and to inhibit the addition of water.

Thus, the present invention relates to a nucleic acid comprising a benzodeazaadenine derivative base represented by the general formula (I):

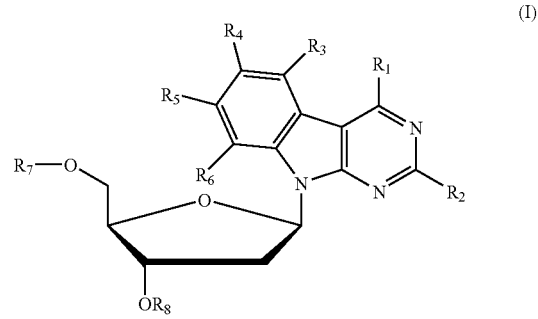

(I)

(wherein $R_1$, $R_2$, $R_3$, $R_4$, $R_5$, and $R_6$ each independently represents a hydrogen atom, an amino group, a mono(lower alkyl)amino group, a di(lower alkyl)amino group, a hydroxyl group, a lower alkoxy group, a halogen, a cyano group, a mercapto group, a lower alkylthio group, or an aryl group, and $R_7$ and $R_8$ each independently represents a hydrogen atom or a phosphate bond group), or a polynucleotide comprising the nucleic acid.

Further, the invention relates to an electronic material comprising the polynucleotide represented by the general formula (I).

The invention provides the nucleic acid comprising the benzodeazaadenine represented by the general formula (I) and the polynucleotide comprising the nucleic acid.

The polynucleotide of the invention can be produced according to the following reaction formula using the nucleic acid of the invention.

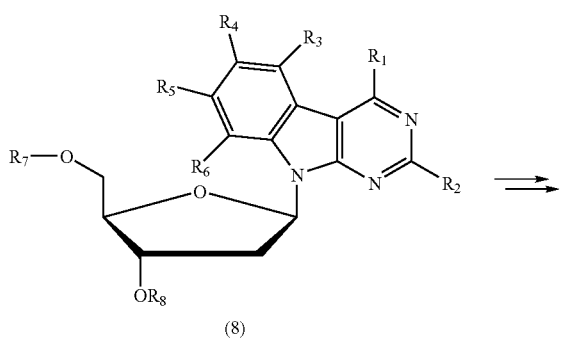

(8)

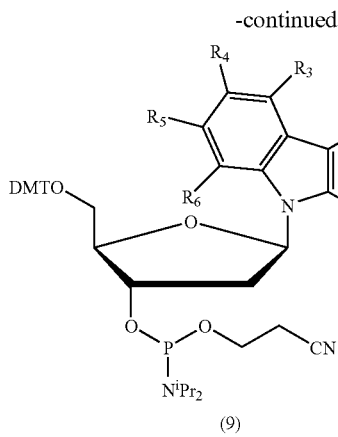

(9)

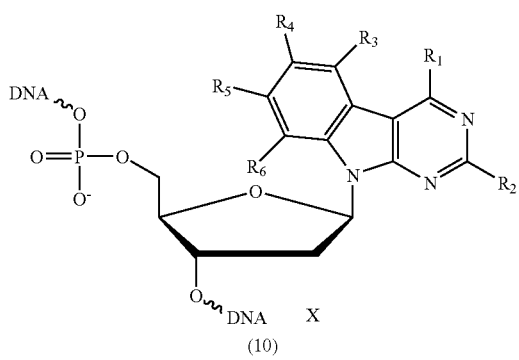

(10)

wherein $R_1$, $R_2$, $R_3$, $R_4$, $R_5$, and $R_6$ are those described above, and $R_7$ and $R_8$ represent hydrogen atoms.

Thus, a reactive derivative such as the phosphoramidite derivative (9) can be produced from the nucleoside (8), and then the derivative can be efficiently converted to a DNA (10) by a DNA synthesis method such as a phosphoramidite method. A plurality of the nucleic acids of the invention can be consecutively introduced into a DNA by such a common DNA synthesis method, and thus-obtained DNA containing the nucleic acid of the invention can achieve efficient hole transport in the DNA.

The invention is more specifically described with reference to an example of the nucleic acid of the invention containing a base in which $R_1$ is a 2-dimethylamino-ethyleneimino group, and $R_2$, $R_3$, $R_4$, $R_5$, and $R_6$ are hydrogen atoms.

A production example of a phosphoramidite derivative (7) of the base is shown below.

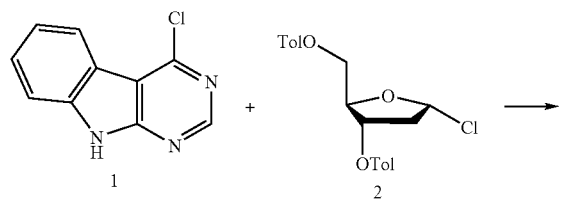

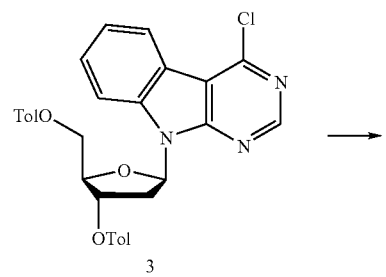

3

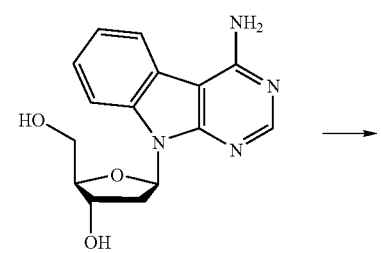

4

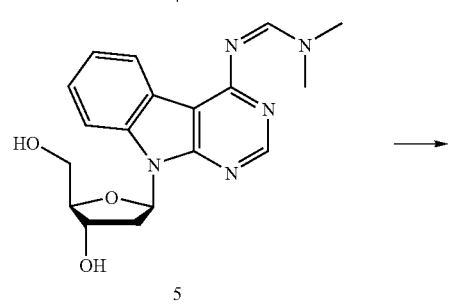

5

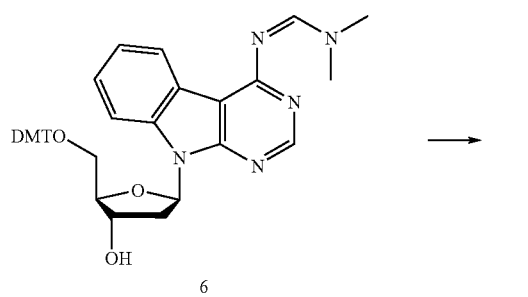

6

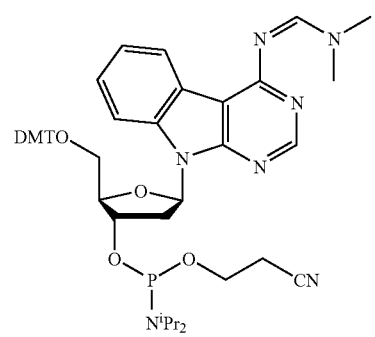

7

A benzodeazaadenine derivative (1) was coupled with a sugar moiety (2) to produce a compound (3), and then the chloro group at the 6-position was converted to an amino group to obtain a compound (4). To incorporate the obtained compound (4) into an oligomer by the phosphoramidite method, protective groups were introduced into the amino group and the hydroxyl group at the 5-position, and the resultant was converted to an amidite to produce the phosphoramidite derivative (7).

The oxidative decomposition rate of thus-produced nucleoside (4) was measured by HPLC using riboflavin as an oxidizing agent and compared with those of the other bases. The results are shown in FIG. 1. In FIG. 1, the abscissa represents time (second) of irradiation with 366 nm light, and the ordinate represents retention ratio (%) of the nucleic acids. In FIG. 1, G represents guanine, A represents adenine, and $^{BD}A$ represents a nucleic acid of the invention.

As a result, though the natural guanine (G) was rapidly decomposed as the irradiation time proceeded, the oxidative decomposition of the nucleic acid $^{BD}A$ of the invention as well as adenine (A) was hardly observed.

Next, an oligomer containing the nucleic acid $^{BD}A$ of the invention was produced by the above-described method, and using the synthesized oligomer, the melting temperature of a duplex was examined to evaluate the base pairing ability of the modified nucleic acid base. As a result, it was shown that the nucleic acid $^{BD}A$ of the invention could form a stable base pair with cytosine or thymine.

Figure 2:
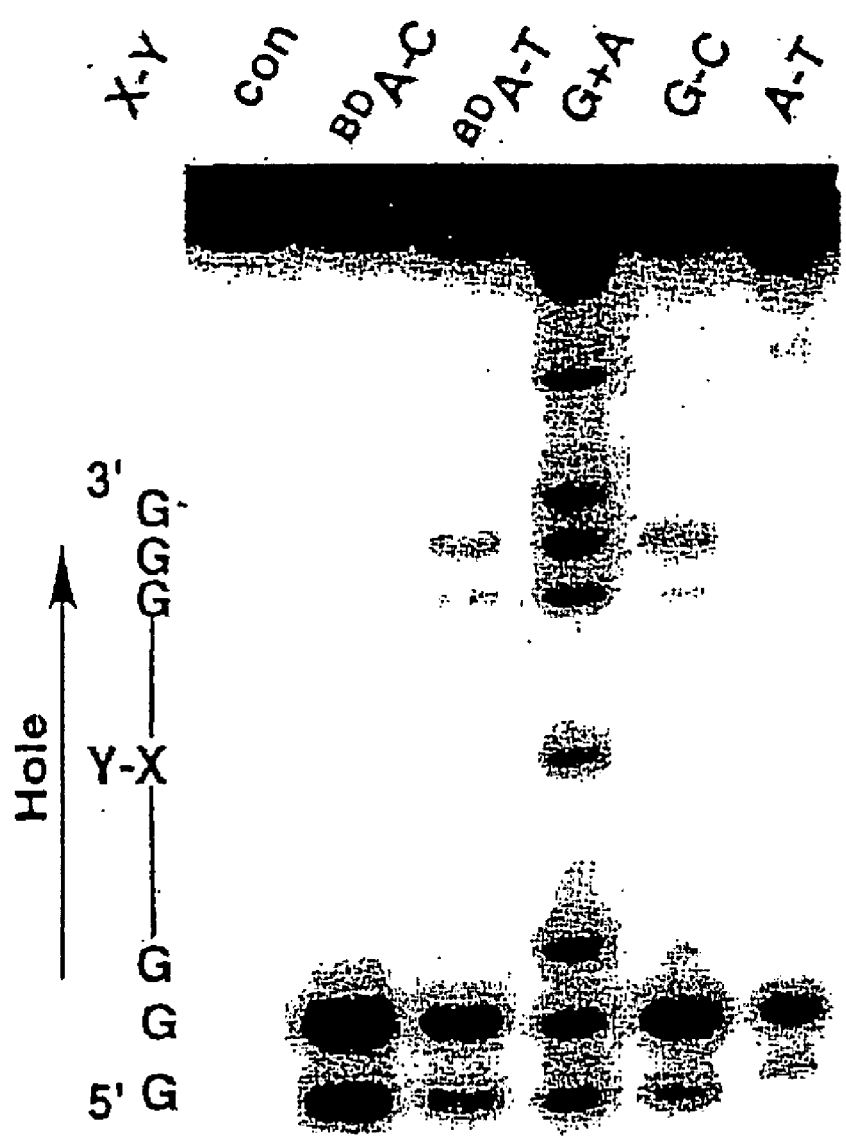
FIG. 2 is a photograph substituted for a drawing showing results of evaluating charge transport in DNAs with a sequence containing a subject base (X) between consecutive guanine (G) sequences.

Then, the charge transportability of the modified nucleic acid base was evaluated by performing charge transport in DNAs with a sequence containing a subject base between consecutive sequences of guanines (G), which are oxidatively decomposed when holes are generated in the hole transport, and cause DNA fragmentation in a subsequent alkali treatment. The results are shown in a photograph of FIG. 2 substituted for a drawing. In FIG. 2, the longitudinal direction is the direction of the hole transport, X represents the base between the guanines (G), and Y represents a base complementary to the base of X. In the transverse direction of FIG. 2, the leftmost is a control (con), and the cases of X-Y of $^{BD}A$-cytosine (C), $^{BD}A$-thymine (T), guanine (G)-adenine (A), guanine (G)-cytosine (C), or adenine (A)-thymine (T) are shown in the right side thereof. In the assay, the samples were irradiated with 312 nm light at 0° C. for 45 minutes in a sodium cacodylate buffer (10 mM, pH 7.0), and subjected to a piperidine treatment at 90° C. for 20 minutes.

As a result, in the case where X was adenine (A) with a low charge transportability, holes were not transported to the consecutive G sequence at the 3' side of X, and fragmentation was observed only in the consecutive G sequence at the 5' side. On the other hand, in the case where X was guanine (G) and the nucleic acid $^{BD}A$ of the invention, holes were transported through G or $^{BD}A$, so that fragmentation was observed also in the consecutive G sequence at the 3' side. As a result of comparing the fragmentation intensities, it became clear that the nucleic acid $^{BD}A$ of the invention had higher charge transportability than that of guanine (G). Further, the charge transport was inhibited when the complementary base was changed from thymine to cytosine.

It was shown by the above results that the nucleic acid $^{BD}A$ of the invention was resistant to the oxidative decomposition, had the charge transportability equal to that of guanine, and thereby could be a modified nucleic acid base composing a DNA wire.

The electronic material of the invention comprises the DNA containing the nucleic acid represented by the general formula (I), preferably a double-stranded DNA. The complementary chain is preferably such that can form common Watson-Crick type base pairs. The nucleic acid of the invention can form a stable base pair with cytosine or thymine, and thus both cytosine and thymine can be used as a complementary base for the nucleic acid of the invention.

Although the holes are smoothly transported in the case of using thymine as the base complementary to the nucleic acid of the invention, the hole transport is inhibited in the case of using cytosine. The on/off control of the hole transport can be achieved utilizing the above fact.

Figure 3:
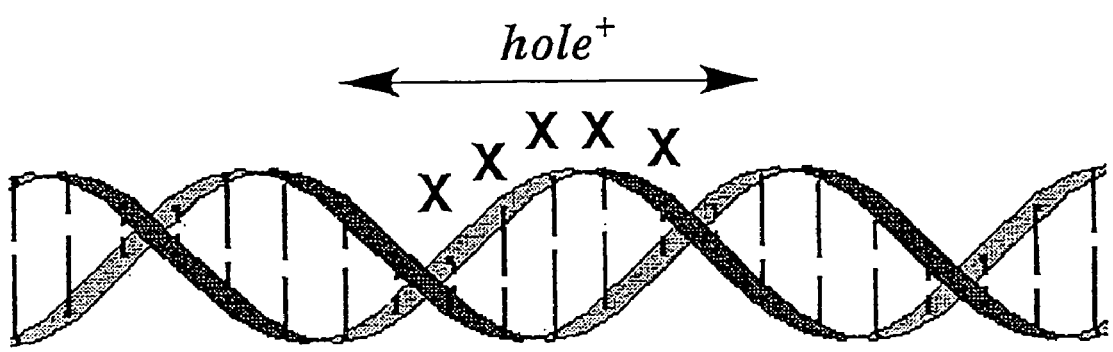
FIG. 3 schematically shows hole transport in a double-stranded DNA of the invention.

An example of the hole transport in the DNA of the invention is schematically shown in FIG. 3. FIG. 3 schematically shows hole transport in a double-stranded DNA of the invention.

In the general formula (I) according to the invention, the lower alkyl group is preferably a straight or branched alkyl group having from 1 to 15 carbon atoms, preferably 1 to 6 carbon atoms, and examples thereof include a methyl group, an ethyl group, etc. The lower alkoxy group preferably comprises a straight or branched lower alkyl group having from 1 to 15 carbon atoms, preferably 1 to 6 carbon atoms, and examples thereof include a methoxy group, an ethoxy group, etc. The aryl group is a monocyclic, polycyclic, or condensed carbocyclic group having from 6 to 30 carbon atoms, preferably 6 to 14 carbon atoms, or a monocyclic, polycyclic, or condensed, 5- to 7-membered, heterocyclic group having at least 1 to 3 nitrogen, oxygen, or sulfur atoms in the ring, and specific examples thereof include a phenyl group, a naphtyl group, a furyl group, a thienyl group, etc. These aryl groups may have a substituent such as a lower alkyl group, a lower alkoxy group, and an amino group.

In the general formula (I), the phosphate bond group includes a phosphate group such as a phosphoramidite group, or a phosphate group to form a DNA.

The nucleic acid of the invention, represented by the general formula (I), shows the charge transportability equal to that of guanine and the low oxidative decomposition rate equal to that of adenine, so that the DNA containing the nucleic acid of the invention is remarkably useful as a conductive nanowire. The DNA of the invention obtained by introducing the artificial nucleic acid base into DNA, which mediates the hole transport in the DNA, is remarkably useful as a next-generation molecular wire usable for (1) DNA nanowires, (2) fluorescent nucleic acid bases, (3) antisense or antigene DNAs for controlling gene expression including DNA replication, RNA transcript, protein recognition, etc., (4) labeled DNAs for hybridization, intended to be used in desired base sequence recognition or single nucleotide polymorphism scan, and (5) molecular logic circuits, biosensors, etc.

EXAMPLES

The present invention will be described in more detail below with reference to Examples without intention of restricting the scope of the invention.

Example 1

Production of 4-chloro-9-(2'-deoxy-β-D-erythro-pentofuranosyl)-9H-pyrimido[4,5-b]indole (Compound 3)

4-chloro-1H-pyrimido[4,5-b]indole (1) (360 mg, 1.77 mmol) was suspended in dry acetonitrile (250 mL) at room temperature. To the suspension was added sodium hydride (60% in oil; 142 mg, 3.54 mmol), and the mixture was refluxed under stirring for 10 minutes. Then, ribose (2) (687 mg, 1.77 mmol) was added thereto and stirred at room temperature for 1 hour. The reaction mixture was concentrated and purified by a column chromatography (silica gel, a hexane solution containing 20% ethyl acetate) to obtain the compound (3) (890 mg, 91% yield).

$^1$H NMR (CDCl$_3$) δ; 38.71 (s, 1H), 8.36 (d, 1H, J=7.9 Hz), 7.99 (d, 2H, J=8.2 Hz), 7.95 (d, 2H, J=6.6 Hz), 7.79 (d, 1H, J=8.4 Hz), 7.37 (dt, 1H, J=8.1, 0.7 Hz), 7.28 (d, 1H, J=8.1 Hz), 7.27 (dt, 1H, J=8.2, 1.1 Hz), 7.23 (d, 2H, J=8.4 Hz), 7.03 (dd, 1H, J=8.8, 6.2 Hz), 5.93 (dt, 1H, J=6.2, 2.7 Hz), 4.86 (dd, 2H, J=11.1, 3.5 Hz), 4.59 (dd, 1H, J=7.2, 3.9 Hz), 3.56 (ddd, 1H, J=16.1, 7.5, 7.2 Hz), 2.59 (ddd, 1H, J=14.4, 6.2, 2.4 Hz), 2.43 (s, 3H), 2.41 (s, 3H);

$^{13}$C NMR (CDCl$_3$) δ; 166.2, 166.1, 155.6, 153.5, 152.7, 144.4, 144.0, 137.8, 129.8, 129.7, 129.3 129.2, 128.3, 126.9, 126.5, 123.4, 122.6, 119.1, 112.8, 112.1, 83.6, 81.8, 74.4, 63.8, 35.3, 21.73, 21.70;

MS (FAB, NBA/CH$_2$Cl$_2$) m/z (%) 556 [(M+H)$^+$]

| HRMS (FAB) | Calculated value for C$_{31}$H$_{27}$ClN$_3$O$_7$ [(M + H)$^+$] | 556.1639, |
|---|---|---|
| | Observed value | 556.1638. |

Example 2

Production of 4-amino-9-(2'-deoxy-β-D-erythro-pentofuranosyl)-9H-pyrimido[4,5-b]indole (Compound 4)

The compound 3 obtained in Example 1 (300 mg, 0.54 mmol) was suspended in 20 mL of methanolic ammonia (saturated at −76° C.), and stirred at 150° C. for 10 hours in a closed vessel. Then, the solution in the vessel was concentrated and purified by a column chromatography (silica gel, a chloroform solution containing 5% methanol) to obtain the compound (4) (117 mg, 72% yield).

$^1$H NMR (DMSO-d$_6$) δ; 38.31 (d, 1H, J=7.7 Hz), 8.27 (s, 1H), 7.84 (d, 1H, J=8.2 Hz), 7.37 (dt, 1H, J=8.2, 1.1 Hz), 7.32–7.25 (3H), 6.82 (dd, 1H, J=8.8, 6.0 Hz), 5.32 (d, 1H, J=4.4 Hz), 5.28 (t, 1H, J=4.9 Hz), 4.46 (m, 1H), 3.86 (dd, 1H, J=7.3, 3.8 Hz), 3.66 (m, 2H), 2.88 (ddd, 1H, J=15.6, 8.8, 6.6 Hz), 2.05 (ddd, 1H, J=15.4, 6.0, 2.2 Hz);

$^{13}$C NMR (DMSO-d$_6$) δ; 157.7, 154.7, 154.4, 135.5, 124.7, 121.3, 121.0, 120.2, 111.8, 87.1, 82.8, 70.9, 61.9, 37.5, 31.5;

MS (FAB, NBA/CH$_2$Cl$_2$) m/z (%) 301 [(M+H)$^+$]

| HRMS (FAB) | Calculated value for C$_{15}$H$_{17}$N$_4$O$_3$ [(M + H)$^+$] | 301.1301 |
|---|---|---|
| | Observed value | 301.1297 |

Example 3

Production of (4-N,N'-dimethylaminomethylidene)amino-9-(2'-deoxy-β-D-erythro-pentofuranosyl)-9H-pyrimido[4,5-b]indole (Compound 5)

N,N-dimethylformamide (5 mL) solution of the compound 4 obtained in Example 2 (130 mg, 0.43 mmol) and N,N-dimethylformamide dimethylacetal (5 mL, 28.3 mmol) was stirred at 55° C. for 18 hours. The reaction mixture was concentrated to obtain a brown oily matter. The oily matter was purified by a column chromatography (silica gel, a chloroform solution containing 10% methanol) to obtain the compound (5) (134 mg, 87% yield).

$^1$H NMR (CDCl$_3$) δ; 38.94 (s, 1H), 8.53 (s, 1H), 8.41 (d, 1H, J=7.1 Hz), 7.49 (d, 1H, J=8.1 Hz), 7.44 (dt, 1H, J=7.1, 1.1 Hz), 7.30 (dt, 1H, J=7.8, 0.9 Hz), 6.73 (dd, 1H, J=8.9, 5.5 Hz), 4.83 (d, 1H, J=5.1 Hz), 4.23 (s, 1H), 4.01 (dd, 1H, J=2.9, 1.4 Hz), 3.82 (m, 1H), 3.31 (s, 3H), 3.29–3.22 (m, 2H), 3.21 (s, 3H), 2.225 (dd, 2H, J=15.4, 5.7 Hz);

$^{13}$C NMR (CDCl$_3$) δ; 161.9, 156.8, 155.2, 153.1, 137.9, 125.9, 123.7, 121.4, 121.0, 108.9, 88.8, 85.7, 74.0, 63.8, 41.2, 39.9, 35.2, 31.4;

MS (FAB, NBA/CH$_2$Cl$_2$) m/z (%) 356 [(M+H)$^+$]

| HRMS (FAB) | Calculated value for C$_{18}$H$_{22}$N$_5$O$_3$ [(M + H)$^+$] | 356.1723 |
|---|---|---|
| | Observed value | 356.1722 |

Example 4

Production of (4-N,N'-dimethylaminomethylidene)amino-9-(2'-deoxy-5'-O-dimethoxytrityl-β-D-erythro-pentofuranosyl)-9H-pyrimido[4,5-b]indole (Compound 6)

The compound 5 obtained in Example 3 (130 mg, 0.37 mmol), 4,4'-dimethoxytrityl chloride (16.1 mg, 0.48 mmol), and 4-dimethylaminopyridine (13 mg, 0.11 mmol) were added to anhydrous pyridine (10 mL), and stirred at room temperature for 2 hours. The reaction mixture was concentrated to obtain a brown oily matter. The oily matter was purified by a column chromatography (silica gel, a mixed solution of 50:50:5 (v/v/v) of hexane, ethyl acetate, and triethylamine) to obtain the compound (6) (66 mg, 33% yield).

$^1$H NMR (CDCl$_3$) δ; 38.91 (s, 1H), 8.53 (s, 1H), 8.39 (d, 1H, J=7.7 Hz), 7.70 (d, 1H, J=8.3 Hz), 7.43 (dd, 2H, J=8.6, 1.5 Hz), 7.31 (dd, 4H, J=9.0, 1.5 Hz), 7.27–7.13 (5H), 6.94 (t, 1H, J=7.3 Hz), 6.75 (dt, 4H, J=9.9, 3.1 Hz), 4.85 (dt, 1H, J=7.7, 4.4 Hz), 4.04 (q, 1H, J=4.6 Hz), 3.747 (s, 3H), 3.745 (s, 3H), 3.48 (d, 1H, J=4.6 Hz), 3.30 (s, 3H), 3.21 (s, 3H), 3.25–3.19 (m, 1H), 2.29 (ddd, 1H, J=13.7, 7.0, 3.8 Hz);

$^{13}$C NMR (CDCl$_3$) δ; 161.3, 158.4, 156.52, 156.47, 154.0, 144.7, 136.8, 135.8, 130.14, 130.11, 128.2, 127.8, 126.8, 125.6, 123.5, 121.8, 121.4, 113.1, 111.7, 105.6, 86.5, 84.5, 82.7, 72.6, 63.6, 60.4, 55.2, 45.6, 41.0, 37.7, 35.1, 21.1, 14.2;

MS (FAB, NBA/CH$_2$Cl$_2$) m/z (%) 658 [(M+H)$^+$]

| HRMS (FAB) | Calculated value for C$_{39}$H$_{40}$N$_5$O$_5$ [(M + H)$^+$] | 658.2951 |
|---|---|---|
| | Observed value | 658.3038 |

Example 5

Production of (4-N,N'-dimethylaminomethylidene)amino-9-(2'-deoxy-5'-O-dimethoxytrityl-β-D-erythro-pentofuranosyl-3'-O-cyanoethyl-N,N'-diisopropylphosphoramidate)-9H-pyrimido[4,5-b]indole (Compound 7)

The compound 6 obtained in Example 4 (10 mg, 15.2 mmol), N,N,N',N'-tetraisopropyl-2-cyanoethyl-diphosphoramidate (5.3 μL, 16.7 mmol), and tetrazole (1.2 mg, 16.7 mmol) were added to acetonitrile (400 μL), and stirred at room temperature for 2 hours. The obtained matter was separated by filtration and used for the next step without further purification.

Example 6

Production of Oligonucleotide

A desired oligonucleotide was produced by a common phosphoramidate method using a nucleotide synthesizer (302 DNA/RNA (Applied Biosystems)). The obtained oligonucleotide was purified by reverse phase HPLC (5-ODS-H column (10×150 mm, 0.1 M triethylamine acetate salt was eluted with the linear gradient of 5 –20% acetonitrile for 30 minutes at pH 7.0 at the flow rate of 3.0 mL/minute)). To identify the produced oligonucleotide, an oligonucleotide containing 2-amino-7-deaza-dA was completely digested at 37° C. for 3 hours using calf intestinal alkaline phosphatase (50 U/mL), snake venom phosphodiesterase (0.15 U/mL), and P1 nuclease (50 U/mL). The digested solution was analyzed by HPLC (COSMOSIL 5C-18AR or Chemcobond 5-ODS-H column (4.6×150 mm, 0.1 M triethylamine acetate salt was eluted with the linear gradient of 0–10% acetonitrile for 20 minutes at pH 7.0 at the flow rate of 1.0 mL/minute)). The concentration of each oligonucleotide was determined by comparing with peaks of a standard solution containing 0.1 mM of dA, dC, dG, and dT.

Example 7

Measurement of Melting Temperature (Tm)

The melting temperature (Tm) of the double-stranded oligonucleotide was measured in a buffer containing 10 mM sodium cacodylate (pH 7.0). The correlation between absorption and temperature was measured at 260 nm using JASCO TPU-550 spectrometer equipped with JASCO TPU-436 temperature control unit. The absorption of the sample was monitored at 260 nm at 2 to 80° C. (temperature rise rate of 1° C./minute). The Tm value was calculated from the result of the measurement.

Example 8

Preparation of 5'-$^{32}$P-end-labeled Primer

A primer for a polymerase elongation reaction (400 pmol of strand concentration) was labeled by a common method of phosphorylation using 4 μL of [γ-$^{32}$P]ATP and 4 μL of T$_4$ polynucleotide kinase. The labeled 5'-end oligonucleotide was collected by ethanol precipitation. The oligonucleotide was purified by 15% non-denaturing gel electrophoresis and isolated by a crash and soak method.

Example 9

Decomposition of 5'-$^{32}$P-end-labeled Oligonucleotide by Light Irradiation in the Presence of Cyanobenzophenones Connected by Oligo-deoxynucleotide A sample solution was prepared by hybridization using a mixture of cooled radioactive-labeled double-stranded oligonucleotides (1 μM) in a sodium phosphate buffer (pH 7.0). The hybridization was achieved by heating the sample to 90° C. for 5 minutes, and then by slowly cooling to room temperature. The double-stranded 5'-$^{32}$P-end-labeled ODN (oligonucleotide) was irradiated with 312 nm light at 0° C. for 60 minutes. After the irradiation, 10 μL of herring sperm DNA, 10 μL of 3 M sodium acetate, and 800 μL of ethanol were added to precipitate all the reaction products. The precipitated DNA was washed with 100 μL of 80% cold ethanol and dried under reduced pressure. The precipitated DNA was dissolved in 50 μL of 10% piperidine, heated at 90° C. for 20 minutes, and concentrated. The radioactivity of the sample was measured by ALOKA 1000 liquid scintillation counter, and the dried DNA pellet was suspended in 80% formamide loading buffer (80% formamide solution of 1 mM EDTA, 0.1% xylenecyanol, and 0.1% Bromophenol Blue). The reactions according to Gilbert-Maxim G+A sequencing reaction were carried out by heating at 90° C. for 3 minutes and by rapidly cooling with ice. The sample (1–2 μL, 2–5×10$^3$ cpm) was placed in a gel of 15% polyacrylamide/7 M urea, electrophoresed at 1900 V for 60 minutes, transferred to a cassette using FUJI X-ray film RX-U, and stored at −80° C. The gel was analyzed by an automatic radiography equipped with a tension meter and by BIO-RAD molecular analysis software (Ver. 2.1). The intensity of the spots obtained by the piperidine treatment was determined by a volume integrator.

INDUSTRIAL APPLICABILITY

The present invention provides the novel artificial nucleic acid base capable of being incorporated into DNAs to form nanowires, in which holes can be freely transported in the DNAs. The nucleic acid base of the invention is more resist to decomposition due to water or oxygen molecules as compared with the natural DNA bases. Further, the fluorescence emission intensity of the base of the invention is changed depending on a base in the complementary chain, so that the base of the invention can be applied for reading base sequence. Furthermore, the nucleic acid base of the invention can form a base pair with a plurality of types of natural bases, and the hole conduction rate is changed depending on the complementary base forming the base pair, whereby the base of the invention can be used for determining the type of the complementary base forming the base pair or for controlling the hole conduction rate.

The invenion claimed is:

1. A nucleic acid represented by the general formula (I):

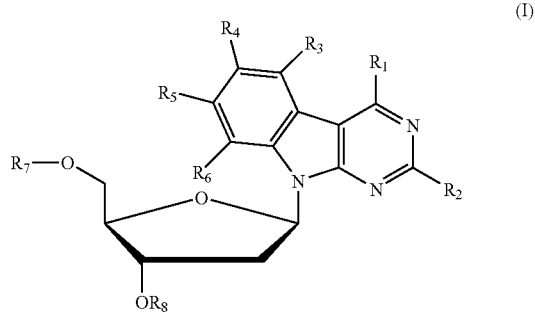

(wherein $R_1$, $R_2$, $R_3$, $R_4$, $R_5$, and $R_6$ each independently represents a hydrogen atom, an amino group, a mono(lower alkyl)amino group, a di(lower alkyl)amino group, a hydroxyl group, a lower alkoxy group, a halogen, a cyano group, a mercapto group, a lower alkylthio group, or an aryl group, and $R_7$ and $R_8$ each independently represents a hydrogen atom or a phosphate bond group), or a polynucleotide comprising the nucleic acid.

2. The nucleic acid according to claim 1, wherein $R_1$ is an amino group, and $R_2$, $R_3$, $R_4$, $R_5$, $R_6$, $R_8$ are hydrogen atoms in the general formula (I).

3. The polynucleotide according to claim 1, wherein the polynucleotide is an oligomer of the nucleic acid represented by the general formula (I).

4. An electronic material comprising the polynucleotide according to claim 1.

5. The polynucleotide according to claim 2, wherein the polynucleotide is an oligomer of the nucleic acid represented by the general formula (I).

6. An electronic material comprising the polynucleotide according to claim 2.

7. An electronic material comprising the polynucleotide according to claim 3.

* * * * *